United States Patent [19]

Ishii et al.

[11] Patent Number: 4,707,460

[45] Date of Patent: Nov. 17, 1987

[54] METHOD FOR REGENERATING PHOSPHORUS-MOLYBDENUM-ALKALI CONTAINING OXIDATION CATALYST

[75] Inventors: Kazuhiro Ishii; Tetsuya Uno; Masaki Kato; Masao Kobayashi, all of Otake, Japan

[73] Assignee: Mitsubishi Rayon Co., Ltd., Tokyo, Japan

[21] Appl. No.: 870,588

[22] Filed: Jun. 4, 1986

[30] Foreign Application Priority Data

Jun. 5, 1985 [JP] Japan .................. 60-122061

[51] Int. Cl.$^4$ .................. B01J 38/66; B01J 27/28; B01J 27/19; C07C 51/235
[52] U.S. Cl. .................. 502/26; 502/24; 502/211; 562/535
[58] Field of Search .................. 502/24, 26, 211, 212; 562/535

[56] References Cited

U.S. PATENT DOCUMENTS

| | | | |
|---|---|---|---|
| 4,000,088 | 12/1976 | Shimizu et al. | 252/437 |
| 4,118,419 | 10/1978 | Ishii et al. | 502/212 |
| 4,165,296 | 8/1979 | Ishii et al. | 502/26 |
| 4,303,550 | 12/1981 | Callahan | 502/24 |
| 4,377,501 | 3/1983 | Khoobiar | 502/211 |
| 4,410,450 | 10/1983 | Sasaki et al. | 502/27 |

FOREIGN PATENT DOCUMENTS

| | | |
|---|---|---|
| 0036057 | 9/1981 | European Pat. Off. . |
| 2229358 | 1/1973 | Fed. Rep. of Germany . |
| 2277062 | 1/1976 | France . |
| 693906 | 7/1953 | United Kingdom . |

*Primary Examiner*—P. E. Konopka
*Attorney, Agent, or Firm*—Armstrong, Nikaido, Marmelstein & Kubovcik

[57] ABSTRACT

A method for regenerating a spent oxidation catalyst useful in the production of unsaturated carboxylic acids by vapor-phase oxidation of unsaturated aldehydes, the catalyst containing, at least, phosphorus, molybdenum, and an alkali metal(s), which method comprises dissolving and/or suspending the spent catalyst in a liquid composition, wherein the contents of ammonium ion and nitrate ion are controlled to be from 7 to 15 moles and from 0.1 to 4.0 moles, respectively, per 12 gram atoms of molybdenum, and immediately thereafter mixing the spent catalyst and the liquid composition.

3 Claims, No Drawings

METHOD FOR REGENERATING PHOSPHORUS-MOLYBDENUM-ALKALI CONTAINING OXIDATION CATALYST

BACKGROUND OF THE INVENTION

The present invention relates to a method for preparing an oxidation catalyst for the production of unsaturated carboxylic acids by vapor-phase oxidation of unsaturated aldehydes.

More particularly, the invention relates to a method for preparing an oxidation catalyst for the production of unsaturated carboxylic acids by vapor-phase oxidation of unsaturated aldehydes, said catalyst containing at least phosphorus, molybdenum and an alkali metal(s) as components, said method comprising dissolving or/and suspending raw materials for the catalyst in water, wherein the contents of ammonium ion and nitrate ion are controlled to be from 7 to 15 moles and from 0.1 to 4.0 moles, respectively, per 12 gram atoms of molybdenum immediately after mixing of all the raw materials that will constitute the catalyst.

A number of catalysts composed mainly of phosphorus and molybdenum or of their alkali metal salts have been proposed for the production of unsaturated carboxylic acids from unsaturated aldehydes by vapor-phase oxidation. For example, catalysts exhibiting excellent efficiency have been proposed by the present inventors in Japanese Patent Publication Nos. 29289/83 and 39138/83. In the preparation of catalysts containing the above-mentioned components, the selection of starting materials is generally important. There are commonly used ammonium paramolybdate as a molybdenum source and orthophosphoric acid as a phosphorus source. Although a method in which molybdenum trioxide is used in place of ammonium paramolybdate is described in an example of Japanese patent application Laid-Open No. 171444/82, this method has industrial disadvantages in that it requires a very long time for the preparation of molybdovanadophosphoric acid and the development of catalytic activity is unstable.

On the other hand, the catalyst often loses its activity during use. While various causes of this deactivation are conceivable, this deactivation is categorized as a type suddenly caused by an abnormal reaction in the course of the normal reaction and a type of gradual deterioration in the catalyst structure during long-term continuous operation. Sometimes the catalyst deterioration occurs before use by heat treatment at excessively high temperatures. It has been proposed that components of deactivated catalyst be recovered by chemical separation and purified to be reused, but this method is industrially uneconomical. There is another attempt to reclaim the deactivated catalyst by adding ammonia or the like to it as such, but the yield of reclamation is still unsatisfactory.

DESCRIPTION OF THE INVENTION

As a result of intensive studies of methods for preparing a phosphorus-molybdenum-alkali type catalyst, the present inventors found that a highly active and highly stable catalyst is obtainable by dissolving or/and suspending raw materials for the catalyst, a deactivated catalyst of the same type, or a mixture of them in water, wherein the contents of ammonium ion and nitrate ion are controlled from 7 to 15 moles and from 0.1 to 4.0 moles, respectively, more preferably from 8 to 12 moles and from 0.4 to 2.0 moles, respectively, per 12 gram atoms of molybdenum, immediately thereafter mixing of all the raw materials that will constitute the catalyst, and treating the solution or suspension as usual. Based on this finding, the present invention has been accomplished.

According to the catalyst preparation method of the present invention, the catalyst can be prepared very easily in a short time by using ammonium paramolybdate, of course, or even by using molybdenum trioxide or compounds including molybdenum like a spent catalyst.

While the effect of the ammonium ion and nitrate ion in reagents used herein, it is conceivable that the ammonium ion may contribute to dissolving the oxides, controlling the pH of the solution, and the formation of pores during the heat treatment, and the nitrate ion may contribute to controlling the pH of the solution, oxidizing reduced parts of the components, and the formation of pores during the heat treatment.

The amounts of ammonium ion and nitrate ion present during the preparation of the catalyst are important, since sufficient catalytic activity cannot be obtained when the amounts are larger or smaller than the respective upper or lower limits defined above.

While the present inventors proposed a method for reclaiming spent catalysts of the present type, which comprises treating them with hydrogen peroxide or ozone (Japanese Patent Publication No. 53572/83), this treatment is not always necessary when the contents of ammonium ion and nitrate ion are controlled to lie in the above defined respective ranges during preparation of the catalyst.

The catalyst preparation method of the present invention is better applied when the starting material is the deactivated catalyst of the same type.

Sometimes volatilization of some components is observed in the deactivated catalyst which has been withdrawn after long-term continuous operation. This tendency is remarkable in particular for molybdenum. When such a deactivated catalyst is used as a raw material, it is supposed that the original activities of the deactivated catalyst will be regenerated by adding the volatilized components as to recover the original atomic ratio. In practice, however, the simple adjustment of the atomic ratio or the treatment with aqueous ammonia does not permit recovering the original degree of activity. Even when a catalyst deactivated by some other reason is chemical-analytically identical in the atomic ratio with the original catalyst, a loss such as pulverization of the catalyst occurs generally during use. In other cases, for instance, when some correction of a deactivated catalyst in its atomic ratio is required by supplementing it with one or more catalyst components, a catalyst having expected efficiency can be reproduced according to the method of the present invention by mixing the deactivated catalyst and desired component materials in water, wherein the contents of ammonium ion and nitrate ion are controlled to lie in the foregoing respective ranges.

The atomic ratio of the catalyst prepared according to the method of the invention is desirably controlled so that, on the basis of gram atoms the proportion of phosphorus and the total proportion of alkali metals will be from 0.5 to 6 and from 0.2 to 6 gram atoms, respectively, and the total proportion of other optional component metals, if they are added, will be from 0.01 to 12 gram atoms.

Metals which can be added as optional components include, for example, As, Cd, In, Sn, Tl, Ca, V, U, Ce, W, Ni, Zr, Ba, Fe, Rh, Mn, Re, Ru, Co, Cu, Al, Si, Cr, Ge, Ti, Nb, Ta, Pb, Zn, Sr, Mg, Ga and Pd.

The means of preparing the catalyst is not particularly restricted but freely chosen from well-known conventional means including evaporation to dryness, precipitation, etc. unless it is accompanied by markedly nonuniform distribution of the component.

Compounds which can be used in combination as raw materials in the catalyst preparation include nitrates, ammonium salts, oxides, and halides of elements, and phosphomolybdic acid and its salts. When the ammonium ion content and/or the nitrate ion content in these raw materials used is out of the range defined in the present invention, the content is adjusted to fall within said range by appropriate addition of aqueous ammonia and/or ammonium nitrate or the like.

Moreover, even when the contents of ammonium ions and nitrate ion in the used raw materials are within the respective ranges defined in the present application, it is preferable to add aqueous ammonia and/or ammonium nitrate to bring these contents to more desirable levels, thereby preparing the catalyst.

A product solidified by evaporation to dryness or by similar operation does not exhibit catalytic function as it is and therefore needs to be subjected to heat treatment under suitable conditions, i.e. at a temperature of 300 to 500° C. for a period of 1 to scores of hours.

The heat-treated catalyst may be used not only as such in molded or powdery form but also in mixture with a diluent. Moreover the catalyst can also be used by itself being supported by a suitable carrier. There is no particular restriction on the diluent provided that it is inert to the present reaction. Such diluents include, for example, silica, alumina, silica-alumina, and silicon carbide.

Unsaturated aldehydes to which the catalyst prepared by the method of the present invention is applicable include, for example, acrolein and methacrolein.

In the vapor-phase oxidation, the ratio of the unsaturated aldehyde to oxygen can be widely varied, while it is desirable that the proportions of the unsaturated aldehyde and oxygen be each in the range of 1 to 20% and the proportion of inert gas be in the range of 60 to 98%. The catalyst prepared according to the present invention is specially suited to achieve high productivity in yielding methacrylic acid from at least 3% concentration of an unsaturated aldehyde (methacrolein).

Normally reactants are charged by themselves diluted with an inert gas such as nitrogen, steam, or carbon dioxide. In particular, the presence of steam is effective in raising the yield of the desired unsaturated carboxylic acid.

The reaction may be carried out under atmospheric pressure or somewhat reduced or elevated pressure, e.g. 0.5 to 20 atm. (absolute pressure).

The reaction temperature can be selected from the range of 240 to 400° C.

EXAMPLES

The present invention is illustrated in more detail with reference to the following examples and comparative examples. In these examples, parts are by weight and the selectivity to unsaturated carboxylic acid represents the molar ratio (%) of the produced unsaturated carboxylic acid to the reacted unsaturated aldehyde.

Unless otherwise noted, catalysts in the examples and comparative examples were evaluated by carrying out the reaction in the following manner: A prescribed amount of the catalyst was filled in a reactor, and a gas mixture of 5% of methacrolein, 10% of oxygen, 30% of steam, and 55% of nitrogen (all vol. %) was passed through the reactor at a prescribed temperature and a space velocity of 2000 1/hr.

EXAMPLE 1

172.9 Parts of molybdenum trioxide was suspended in 400 parts of water and 60 parts of 28% aqueous ammonia and 8 parts of ammonium nitrate were added to the suspension. To this mixture were successively added 11.5 parts of 85% orthophosphoric acid, 7.05 parts of 60% orthoarsenic acid, 4.55 parts of vanadium pentoxide, and 9.75 parts of cesium nitrate. In the resulting slurry, the proportions of ammonium ion and nitrate ion were 10.9 moles and 1.5 moles, respectively, to 12 gram atoms of Mo. This slurry was evaporated with stirring to dryness. The obtained solid was dried at 130° C. for 16 hours, finely pulverized, compression-molded, and calcined at 400° C. for 5 hours in a stream of air. The metallic element ratio in the thus obtained catalyst is represented by $P_1Mo_{12}As_{0.3}V_{0.5}$.

Results of the reaction conducted to evaluate this catalyst are shown in Table 1 later, revealing that this catalyst exhibits efficiency equivalent to that of the highly active catalyst prepared in Example 3 according to a conventional method using ammonium paramolybdate. The space time yield of methacrylic acid (the amount of methacrylic acid produced per 1l of catalyst per 1 hr.) in this case (Example 1) was very high, as high as 2.46 ml/l·hr.

EXAMPLE 2

The reaction was conducted by using a portion of the catalyst of Example 1 under the same conditions as stated above except that the concentration of methacrolein in the feed gas was lowered to 4%. Results of the reaction were as shown in Table 1. In this case, the percentage of reacted methacrolein was 67.6%, which is 5.3 points higher than that given in the case where the concentration of methacrolein is 5%, while the space time yield of methacrylic acid decreased to 2.12 ml/l·hr. Although this productivity is considerably high, the means of raising the percentage of reacted methacrolein by lowering its concentration in the feed is not always profitable in view of methacrylic acid productivity.

EXAMPLE 3

A catalyst was prepared in the same manner as in Example 1 except that 212 parts of ammonium paramolybdate was used in place of molybdenum trioxide and none of aqueous ammonia and ammonium nitrate were used. In this case, said proportions (to 12 gram atoms of molybdenum, in slurried mixture of all the raw materials) of ammonium ion and nitrate ion were 10.3 moles and 0.5 mole, respectively. Results of the reaction conducted to evaluate this catalyst are shown in Table 1.

COMPARATIVE EXAMPLE 1

A catalyst was prepared in the same manner as in Example 1 but using none of aqueous ammonia and ammonium nitrate. In this case, said proportions of ammonium ion and nitrate ion were zero and 0.5 mole per 12 gram atoms of molybdenum, respectively. Results of the reaction conducted to evaluate this catalyst are shown in Table 1. This catalyst was much inferior in efficiency to the catalyst of Example 1.

COMPARATIVE EXAMPLE 2

A catalyst was prepared in the same manner as in Example 1 but using no aqueous ammonia. Said proportions of ammonium ion and nitrate ion in this case, were 1.0 mole and 1.5 moles, per 12 gram atoms of molybdenum, respectively. Results of the reaction conducted to evaluate this catalyst, as shown in Table 1, have proved that this catalyst is considerably inferior in efficiency to the catalyst of Example 1. It can be seen that even when ammonium ion and nitrate ion are present in the feed material mixture, the efficiency of the resulting catalyst will be low if the amounts of these ions are improper.

COMPARATIVE EXAMPLE 3

A catalyst was prepared in the same manner as in Example 1 but using 200 parts of aqueous ammonia. In this case, said proportions of ammonium ion and nitrate ion were 33.9 moles and 1.5 moles per 12 gram atoms of molybdenum, respectively. Results of the reaction conducted to evaluate this catalyst, as shown in Table 1, have proved that this catalyst is inferior in efficiency to the catalyst of Example 1. It can be seen that excessive ammonium ion lower the efficiency of the resulting catalyst.

COMPARATIVE EXAMPLE 4

A catalyst was prepared in the same manner as in Example 1 but using 30 parts of ammonium nitrate. In this case, said proportions of ammonium ion and nitrate ion were 13.6 moles and 4.3 moles per 12 gram atoms of molybdenum, respectively. Results of the reaction conducted to evaluate this catalyst, as shown in Table 1, have proved that this catalyst is inferior in efficiency to the catalyst of Example 1. It can be seen that excessive nitrate ion lower the efficiency of the resulting catalyst.

TABLE 1

| | Reaction temperature (°C.) | Percentage of reacted methacrolein | Selectivity to methacrylic acid (%) | Space time yield of methacrylic acid (ml/l · hr) |
|---|---|---|---|---|
| Example 1 | 280 | 62.3 | 88.4 | 2.46 |
| Example 2 | 280 | 67.6 | 88.0 | 2.12 |
| Example 3 | 280 | 63.1 | 87.2 | 2.45 |
| Comparative Example 1 | 280 | 25.5 | 77.9 | 0.89 |
| Comparative Example 2 | 280 | 33.5 | 84.9 | 1.27 |
| Comparative Example 3 | 280 | 45.3 | 87.7 | 1.77 |
| Comparative Example 4 | 280 | 38.6 | 86.6 | 1.49 |

EXAMPLE 4

A portion of the catalyst prepared in Example 1 was deactivated by raising intentionally the reaction temperature under continuous operation of the reaction to cause an abnormal reaction. Results of the reaction conducted by using this deactivated catalyst are shown in Table 2. 200 Parts of this deactivated catalyst was dispersed (partially dissolved) in 500 parts of water, then 10 parts of ammonium nitrate and 50 parts of 28% aqueous ammonia were added to the dispersion, and the mixture was evaporated with stirring to dryness. In this case, said proportions of ammonium ion and nitrate ion were 9.1 moles and 1.2 moles per 12 gram atoms of molybdenum, respectively. The obtained solid mass was finely pulverized, compression-molded, and calcined at 400° C. for 5 hours in a stream of air, thus yielding a regenerated catalyst.

Results of the reaction conducted to evaluate this regenerated catalyst are shown in Table 2. This catalyst exhibited efficiency equal to that of the catalyst prepared in Example 1.

COMPARATIVE EXAMPLE 5

A catalyst was prepared in the same manner as in Example 4 but without using aqueous ammonia. In this case, said proportions of ammonium ion and nitrate ion were 1.2 moles each. Results of the reaction conducted to evaluate this catalyst are shown in Table 2.

COMPARATIVE EXAMPLE 6

A catalyst was prepared in the same manner as in Example 4 but without using ammonium nitrate. In this case, said proportion of ammonium ion was 7.9 moles per 12 gram atoms of molybdenum but the proportion of nitrate ion was zero. Results of the reaction conducted to evaluate this catalyst are shown in Table 2.

COMPARATIVE EXAMPLE 7

A catalyst was prepared in the same manner as in Example 4 but without using any of ammonium nitrate and aqueous ammonia. In this case, the aqueous dispersion contained neither ammonium ion nor nitrate ion. Results of the reaction conducted to evaluate this catalyst are shown in Table 2.

COMPARATIVE EXAMPLE 8

A catalyst was prepared in the same manner as in Example 4 but using 200 parts of 28% aqueous ammonia. In this case, said proportions of ammonium ion and nitrate ion were 32.9 moles and 1.2 moles, respectively. Results of the reaction conducted to evaluate this catalyst are shown in Table 2.

COMPARATIVE EXAMPLE 9

A catalyst was prepared in the same manner as in Example 4 but using 40 parts of ammonium nitrate. In this case, said proportions of ammonium ion and nitrate ion were 12.7 moles and 4.8 moles, respectively. Results of the reaction conducted to evaluate this catalyst are shown in Table 2.

TABLE 2

| | Reaction temperature (°C.) | Percentage of reacted methacrolein | Selectivity to methacrylic acid (%) |
|---|---|---|---|
| Example 4 (deactivated catalyst) | 280 | 12.3 | 75.9 |
| Example 4 (regenerated catalyst) | 280 | 62.9 | 88.7 |
| Comparative Example 5 | 280 | 35.9 | 85.6 |
| Comparative Example 6 | 280 | 51.7 | 85.5 |
| Comparative Example 7 | 280 | 22.2 | 88.8 |
| Comparative Example 8 | 280 | 46.1 | 87.5 |
| Comparative Example 9 | 280 | 34.2 | 86.1 |

EXAMPLE 5

A part of the catalyst prepared in Example 1 was calcined at 600° C. for 3 hours. Results of the reaction conducted to evaluate this deactivated catalyst are shown in Table 3 (deactivated catalyst).

A catalyst was prepared from this deactivated catalyst according to the reclamation procedure of Example 4. In this case, said proportions of ammonium ion and nitrate ion were 9.1 moles and 1.2 moles, respectively. Results of the reaction conducted to evaluate this regenerated catalyst are shown in Table 3 (regenerated catalyst).

TABLE 3

|  | Reaction temperature (°C.) | Percentage of reacted methacrolein | Selectivity to methacrylic acid (%) |
| --- | --- | --- | --- |
| Example 5 (deactivated catalyst) | 280 | 11.3 | 73.6 |
| Example 5 (regenerated catalyst) | 280 | 61.3 | 89.0 |

EXAMPLE 6

A portion of the catalyst prepared in Example 1 was used continuously for the reaction during 150 days. The catalyst used for 150 days gave a percentage reacted methacrolein of 49.3% and a methacrylic acid selectivity of 82.4% at 330° C., thus indicating performance characteristics considerably lowered as compared with the initial levels thereof.

This catalyst was withdrawn and treated according to the reclamation procedure of Example 4, preparing a regenerated catalyst. In this case, said proportions of ammonium ion and nitrate ion were 9.4 moles and 1.2 moles, respectively. The reaction conducted at 280° C. to evaluate this regenerated catalyst gave a percentage reacted methacrolein of 58.8% and a methacrylic acid selectivity 88.1%, indicating that the catalyst had been greatly improved in activity and selectivity.

Composition analysis showed that comparing with the original catalyst, this catalyst had lost molybdenum by 3.5% on account of volatilization and the difference in contents of the other components was within the range of analysis errors. Accordingly, a catalyst was further prepared by adding ammonium paramolybdate in an amount corresponding to that of volatilized molybdenum to the deactivated catalyst and following the reclamation procedure of Example 4. The reaction conducted at 280° C. to evaluate this catalyst gave a percentage reacted methacrolein of 62.8% and a methacrylic acid selectivity of 88.2%. These performance characteristics are nearly equal to those of the original catalyst.

EXAMPLE 7

106 Parts of ammonium paramolybdate was dissolved in 450 parts of water, and to this solution were added successively 5.8 parts of 85% orthophophoric acid, 3.53 parts of 60% orthoarsenic acid, 2.28 parts of vanadium pentoxide, and 4.86 parts of cesium nitrate. To the resulting slurry were further added 100 parts of the catalyst deactivated in Example 4, 30 parts of 28% aqueous ammonia, and 5 parts of 60% nitric acid. The mixture was evaporated with stirring to dryness. In this case, said proportions of ammonium ion and nitrate ion in the resulting slurry before evaporation were 9.9 moles and 0.7 mole, respectively. The obtained solid mass was finely pulverized, compression-molded, and calcined at 400° C. for 5 hours in a stream of air. The reaction to evaluate the thus obtained catalyst was conducted at 280° C. with the result that the percentage of reacted methacrolein was 63.3% and the selectivity to methacrylic acid was 87.4%.

EXAMPLES 8-10

Catalysts of compositions as shown in Table 4 (high-activity catalysts) were prepared according to the procedure of Example 2. These catalysts were deactivated by raising intentionally the reaction temperature under continuous operation of the reaction to cause an abnormal reaction (deactivated catalysts). Catalysts were prepared according to the reclamation procedure of Example 4 (regenerated catalysts). Results of the reaction conducted to evaluated these catalysts are shown in Table 4.

TABLE 4

|  | Elements of catalyst and atomic ratio | Catalyst nature | Reaction temperature (°C.) | Percentage of reacted methacrolein | Selectivity to methacrylic acid (%) |
| --- | --- | --- | --- | --- | --- |
| Example 8 | $P_{1.5}Mo_{12}K_1Cu_{0.3}Mg_1Sb_{0.8}$ | High-activity catalyst | 290 | 60.4 | 85.2 |
|  |  | Deactivated catalyst | 330 | 45.5 | 81.9 |
|  |  | Regenerated catalyst | 290 | 59.8 | 86.4 |
| Example 9 | $P_2Mo_{12}Rh_1Cs_1V_{0.3}Cr_{0.8}Fe_{0.2}$ | High-activity catalyst | 290 | 56.7 | 87.4 |
|  |  | Deactivated catalyst | 330 | 31.3 | 85.5 |
|  |  | Regenerated catalyst | 290 | 57.9 | 87.6 |
| Example 10 | $P_1Mo_{12}K_{0.8}Ge_{0.5}Sb_{0.2}Rh_{0.01}$ | High-activity catalyst | 280 | 55.2 | 88.6 |
|  |  | Deactivated catalyst | 330 | 40.9 | 80.2 |
|  |  | Regenerated catalyst | 280 | 56.1 | 86.8 |

The following table shows amounts of ammonium ion and nitrate ion per 12 gram atoms of Mo during perparations of high-activity catalysts and regenerated catalysts in the above three examples.

|  |  | Ammonium ions | Nitrate ions |
| --- | --- | --- | --- |
| Example 8 | High-activity catalyst | 10.3 moles | 3.6 moles |
|  | Regenerated catalyst | 9.7 moles | 1.3 moles |

-continued

|  |  | Ammonium ions | Nitrate ions |
|---|---|---|---|
| Example 9 | High-activity catalyst | 10.3 moles | 2.6 moles |
|  | Regenerated catalyst | 10.4 moles | 1.4 moles |
| Example 10 | High-activity catalyst | 10.3 moles | 0.8 mole |
|  | Regenerated catalyst | 9.0 moles | 1.2 moles |

What is claimed is:

1. A method for regenerating a deactivated oxidation catalyst for the vapor-phase catalytic oxidation of unsaturated aldehydes to unsaturated carboxylic acids, said catalyst containing phosphorus, molybdenum and at least one alkali metal, wherein the proportion of phosphorus is 0.5–6 gram atoms based on 12 gram atoms of molybdenum, and the proportion of alkali metal is 0.2–6 gram atoms based on 12 gram atoms of molybdenum, said method comprising the steps of mixing the deactivated catalyst with a liquid composition consisting essentially of water, ammonium ion and nitrate ion, wherein the contents of ammonium ion and nitrate ion are controlled to be from 7 to 15 moles and from 0.1 to 4.0 moles, respectively, per 12 gram atoms of molybdenum, removing said liquid composition by drying, and calcining the obtained dried catalyst.

2. A method for regenerating a deactivated oxidation catalyst as in claim 1, wherein the catalyst contains at least one additional element in a proportion of 0.01 to 12 gram atoms per 12 gram atoms of molybdenum, said additional element being selected from the group consisting of As, Cd, In, Sn, Tl, Ca, V, U, Ce, W, Ni, Zr, Ba, Fe, Rh, Mn, Re, Ru, Co, Cu, Al, Si, Cr, Ge, Ti, Nb, Ta, Pb, Zn, Sr, Mg, Ga, and Pd.

3. A method for regenerating a deactivated oxidation catalyst for the vapor-phase catalytic oxidation of unsaturated aldehydes to unsaturated carboxylic acids, said catalyst containing phosphorus, molybdenum and at least one alkali metal, wherein the proportion of phosphorus is 0.5–6 gram atoms based on 12 gram atoms of molybdenum, and the proportion of alkali metal is 0.2–6 gram atoms based on 12 gram atoms of molybdenum, said method comprising the steps of mixing a mixture consisting essentially of the deactivated catalyst and salts and/or oxides of elements in which the deactivated catalyst is deficient with a liquid composition consisting essentially of water, ammonium ion and nitrate ion, wherein the contents of ammonium ion and nitrate ion are controlled to be from 7 to 15 moles and from 0.1 to 4.0 moles, respectively, per 12 gram atoms of molybdenum, removing said liquid composition by drying, and calcining the obtained dried catalyst.

* * * * *